United States Patent
Silverberg et al.

(10) Patent No.: US 12,310,890 B2
(45) Date of Patent: *May 27, 2025

(54) PUNCTAL PLUG AND BIOADHESIVES

(71) Applicant: OCULAR THERAPEUTIX, INC., Bedford, MA (US)

(72) Inventors: Noah Silverberg, Santa Barbara, CA (US); Mark Silverberg, Santa Barbara, CA (US)

(73) Assignee: Ocular Therapeutix, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/387,612

(22) Filed: Nov. 7, 2023

(65) Prior Publication Data
US 2024/0148553 A1     May 9, 2024

Related U.S. Application Data

(63) Continuation of application No. 17/896,434, filed on Aug. 26, 2022, now Pat. No. 12,150,896, which is a
(Continued)

(51) Int. Cl.
*A61F 9/007*     (2006.01)
*A61K 9/00*      (2006.01)
(Continued)

(52) U.S. Cl.
CPC .......... *A61F 9/00772* (2013.01); *A61L 31/04* (2013.01); *A61L 31/148* (2013.01); *A61K 9/0048* (2013.01); *A61L 2430/16* (2013.01)

(58) Field of Classification Search
CPC .... A61F 9/00772; A61L 31/04; A61K 9/0048
See application file for complete search history.

(56) References Cited

U.S. PATENT DOCUMENTS

| 3,949,750 A | 4/1976 | Freeman |
| 3,993,071 A | 11/1976 | Higuchi et al. |
| (Continued) | | |

FOREIGN PATENT DOCUMENTS

| KR | 20070121537 | 12/2007 |
| WO | 2009/008946 | 1/2009 |
| (Continued) | | |

OTHER PUBLICATIONS

International Search Report and Written Opinion for International Application No. PCT/US2016/055993 mailed Dec. 22, 2016.
(Continued)

*Primary Examiner* — Jessica Arble
*Assistant Examiner* — Nhu Q. Tran
(74) *Attorney, Agent, or Firm* — LOWENSTEIN SANDLER LLP

(57) ABSTRACT

The present disclosure provides devices and methods for the treatment of ophthalmological conditions such as dry eye. Among the devices provided are punctal plugs and devices for inserting punctal plugs. The punctal plugs may be shaped for insertion in the punctum and/or the canaliculus. They may also be coated with a bioadhesive. Methods for inserting the punctal plugs are provided, as well as methods for preparing bioadhesive-coated punctal plugs. A method is also provided to treat dry-eye using a bioadhesive without use of a punctal plug.

2 Claims, 1 Drawing Sheet

Related U.S. Application Data continuation of application No. 15/766,647, filed as application No. PCT/US2016/055993 on Oct. 7, 2016, now Pat. No. 11,458,041.

(60) Provisional application No. 62/239,006, filed on Oct. 8, 2015.

(51) Int. Cl.
*A61L 31/04* (2006.01)
*A61L 31/14* (2006.01)

(56) References Cited

U.S. PATENT DOCUMENTS

| | | |
|---|---|---|
| 4,915,684 A | 4/1990 | MacKeen et al. |
| 5,283,063 A | 2/1994 | Freeman |
| 5,469,867 A | 11/1995 | Schmitt |
| 5,902,598 A | 5/1999 | Chen et al. |
| 6,027,470 A | 2/2000 | Mendius |
| 6,196,993 B1 | 3/2001 | Cohan et al. |
| 6,437,152 B1 | 8/2002 | Jackson et al. |
| 6,509,327 B1 | 1/2003 | Cagle et al. |
| 6,646,001 B2 | 11/2003 | Hellberg et al. |
| 6,982,090 B2 | 6/2006 | Gillespie |
| 7,109,371 B2 | 9/2006 | Clissold et al. |
| 7,166,730 B2 | 1/2007 | Nisnevich et al. |
| 7,897,795 B2 | 3/2011 | Henschke et al. |
| 7,998,497 B2 | 8/2011 | de Juan, Jr. et al. |
| 8,080,593 B2 | 12/2011 | Humayun et al. |
| 8,178,582 B2 | 5/2012 | Kabra |
| 8,268,299 B2 | 9/2012 | Kabra et al. |
| 8,323,630 B2 | 12/2012 | Kabra et al. |
| 8,388,941 B2 | 3/2013 | Chowhan et al. |
| 8,409,606 B2 | 4/2013 | Sawhney et al. |
| 8,436,194 B2 | 5/2013 | Henschke et al. |
| 8,476,471 B2 | 7/2013 | Mannikouros et al. |
| 8,512,749 B2 | 8/2013 | Edelman et al. |
| 8,535,705 B2 | 9/2013 | Edelman et al. |
| 8,563,027 B2 | 10/2013 | Sawhney et al. |
| 8,691,265 B2 | 4/2014 | de Juan et al. |
| 8,715,712 B2 | 5/2014 | de Juan et al. |
| 8,722,735 B2 | 5/2014 | Kabra et al. |
| 8,742,143 B2 | 6/2014 | Henschke et al. |
| 8,747,884 B2 | 6/2014 | de Juan et al. |
| 8,754,123 B2 | 6/2014 | Kabra |
| 8,846,073 B2 | 9/2014 | Spada et al. |
| 8,900,662 B2 | 12/2014 | Lee et al. |
| 8,901,319 B2 | 12/2014 | Chambournier et al. |
| 8,957,240 B2 | 2/2015 | Hogan et al. |
| 8,961,501 B2 | 2/2015 | Jarrett et al. |
| 9,061,065 B2 | 6/2015 | Robinson et al. |
| 9,115,109 B2 | 8/2015 | Wei et al. |
| 9,125,807 B2 | 9/2015 | Sawhney et al. |
| 9,126,898 B2 | 9/2015 | Oh et al. |
| 9,144,561 B2 | 9/2015 | Kabra |
| 9,149,428 B2 | 10/2015 | Spada et al. |
| 9,168,222 B2 | 10/2015 | de Juan et al. |
| 9,187,593 B2 | 11/2015 | Dadey et al. |
| 9,205,150 B2 | 12/2015 | El-Hayek et al. |
| 9,212,125 B2 | 12/2015 | Kardos et al. |
| 9,254,267 B2 | 2/2016 | Sawhney |
| 9,290,432 B2 | 3/2016 | Bischof et al. |
| 9,370,485 B2 | 6/2016 | Sawhney et al. |
| 9,393,223 B2 | 7/2016 | Hughes |
| 9,421,126 B2 | 8/2016 | Alster et al. |
| 9,445,944 B2 | 9/2016 | Rapacki et al. |
| 9,463,114 B2 | 10/2016 | Odrich et al. |
| 9,464,028 B2 | 10/2016 | Wei et al. |
| 9,504,696 B2 | 11/2016 | Robinson et al. |
| 9,540,311 B2 | 1/2017 | Wei et al. |
| 9,549,852 B2 | 1/2017 | de Juan et al. |
| 9,555,045 B2 | 1/2017 | Garrigue et al. |
| 9,561,282 B2 | 2/2017 | Dadey et al. |
| 9,707,173 B2 | 7/2017 | Kabra |
| 9,707,238 B2 | 7/2017 | Chang et al. |
| 9,750,636 B2 | 9/2017 | Rubin et al. |
| 9,775,906 B2 | 10/2017 | Sawhney et al. |
| 9,828,356 B2 | 11/2017 | Wei et al. |
| 9,849,082 B2 | 12/2017 | de Juan, Jr. et al. |
| 9,937,073 B2 | 4/2018 | de Juan et al. |
| 9,949,942 B2 | 4/2018 | Butuner |
| 10,004,636 B2 | 6/2018 | Alster et al. |
| 10,064,872 B2 | 9/2018 | Chang et al. |
| 10,100,028 B2 | 10/2018 | Mannikouros et al. |
| 10,226,417 B2 | 3/2019 | Jarrett et al. |
| 10,245,178 B1 | 4/2019 | Heitzmann et al. |
| 10,251,954 B2 | 4/2019 | Sawhney et al. |
| 10,278,919 B2 | 5/2019 | Robinson et al. |
| 10,300,014 B2 | 5/2019 | de Juan, Jr. et al. |
| 10,383,817 B2 | 8/2019 | de Juan et al. |
| 10,420,724 B2 | 9/2019 | Jarrett et al. |
| 10,434,009 B2 | 10/2019 | Rapacki et al. |
| 10,441,543 B2 | 10/2019 | Spada et al. |
| 10,456,293 B2 | 10/2019 | Rubin et al. |
| 10,617,563 B2 | 4/2020 | Jarrett et al. |
| 10,736,774 B2 | 8/2020 | Alster et al. |
| 10,744,099 B2 | 8/2020 | Ibin et al. |
| 10,786,462 B2 | 9/2020 | Jarrett et al. |
| 10,835,416 B2 | 11/2020 | de Juan et al. |
| 10,849,656 B2 | 12/2020 | Navratil et al. |
| 10,864,218 B2 | 12/2020 | Hughes |
| 10,874,606 B2 | 12/2020 | de Juan, Jr. et al. |
| 10,905,765 B2 | 2/2021 | Jarrett et al. |
| 11,458,041 B2 | 10/2022 | Silverberg et al. |
| 11,559,429 B1 | 1/2023 | Silverberg et al. |
| 2002/0169409 A1 | 11/2002 | Gillespie |
| 2003/0065060 A1 | 4/2003 | Qvist et al. |
| 2003/0108511 A1 | 6/2003 | Sawhney |
| 2004/0175410 A1 | 9/2004 | Ashton et al. |
| 2005/0197614 A1 | 9/2005 | Pritchard et al. |
| 2005/0232972 A1 | 10/2005 | Odrich |
| 2005/0283109 A1 | 12/2005 | Peyman |
| 2006/0095108 A1 | 5/2006 | Chowdhury et al. |
| 2007/0298075 A1 | 12/2007 | Borgia et al. |
| 2008/0045911 A1 | 2/2008 | Borgia et al. |
| 2008/0124400 A1 | 5/2008 | Liggins et al. |
| 2008/0140192 A1 | 6/2008 | Humayun et al. |
| 2008/0247984 A1 | 10/2008 | Messersmith et al. |
| 2009/0227981 A1 | 9/2009 | Bennett |
| 2009/0234384 A1 | 9/2009 | Hadba |
| 2010/0209478 A1 | 8/2010 | Sawhney et al. |
| 2010/0239635 A1 | 9/2010 | McClain et al. |
| 2010/0278898 A1 | 11/2010 | Hughes et al. |
| 2012/0059338 A1 | 3/2012 | Beeley et al. |
| 2012/0156259 A1 | 6/2012 | Rau et al. |
| 2014/0121612 A1 | 5/2014 | Rubin et al. |
| 2014/0128478 A1 | 5/2014 | Asgharian et al. |
| 2014/0371308 A1 | 12/2014 | Hughes |
| 2015/0272898 A1 | 10/2015 | Hughes et al. |
| 2015/0374633 A1 | 12/2015 | Fedorchak et al. |
| 2016/0296627 A1 | 10/2016 | Garcia et al. |
| 2016/0354309 A1 | 12/2016 | Heitzmann et al. |
| 2017/0037002 A1 | 2/2017 | Vajda et al. |
| 2017/0073323 A1 | 3/2017 | Wei et al. |
| 2017/0224356 A1 | 8/2017 | Becker |
| 2017/0296483 A1 | 10/2017 | Barman et al. |
| 2018/0085307 A1 | 3/2018 | Sawhney et al. |
| 2019/0021991 A9 | 1/2019 | Heitzmann et al. |
| 2019/0038636 A1 | 2/2019 | Vrabec |
| 2019/0216727 A1 | 7/2019 | Odrich et al. |
| 2019/0224046 A1 | 7/2019 | Heitzmann et al. |
| 2020/0038326 A1 | 2/2020 | Spada et al. |
| 2020/0138701 A9 | 5/2020 | Odrich et al. |
| 2020/0246222 A1 | 8/2020 | Malanga et al. |
| 2020/0345544 A1 | 11/2020 | Ketelson et al. |
| 2020/0345750 A1 | 11/2020 | Chang et al. |
| 2020/0383915 A1 | 12/2020 | Jablonski et al. |

FOREIGN PATENT DOCUMENTS

| | | |
|---|---|---|
| WO | 2010/093873 | 8/2010 |
| WO | 2010111449 A1 | 9/2010 |
| WO | 2013/086015 | 6/2013 |
| WO | 2016/094646 | 6/2016 |

(56) References Cited

FOREIGN PATENT DOCUMENTS

| WO | 2016/183296 | 11/2016 |
|----|-------------|---------|
| WO | 2017/015591 | 1/2017  |
| WO | 2017/091749 | 6/2017  |
| WO | 2018/058048 | 3/2018  |

OTHER PUBLICATIONS

Pardo-Lopez et al., "Anterior chamber migration of dexametasona intravitreal implant (Ozurdex)", Graefe's Archive for Clinical and Experimental Opthalmology, Nov. 2011, vol. 250, pp. 1703-1704, Published by Springer.
Gillies et al., "A Randomized Clinical Trial of Intravitreal Bevacizumab versus Intravitreal Dexamethasone for Diabetic Macular Edema", American Academy of Opthamology, 2014, pp. 2473-2481, Published by Elsevier Inc.
Carter et al., "Size Variation of the Lacrimal Punctum in Adults", Opthalmic Plastic and Reconstructive Surgery 4(4): pp. 231-233, 1988.
Tyson et al., "Punctum and canalicular anatomy for hydrogel-based intracanalicular insert technology", Therapeutic Delivery 11(3), pp. 173-182, 2020.
Potvin et al., "Cataract surgery and methods of wound closure: A Review", Clinical Ophthalmology, 2015, vol. 921.
Trujillo et al., "Ocular adhesives: Design, chemistry, crosslinking mechanisms, and applications", Biomaterials, 6 2019, pp. 345-367, vol. 197.
Bethke, Walter, "Ocular Sealants and Glues in Review", Review of Ophthalmology, 2014.
Ricci et al., "Octyl 2-cyanoacrylate tissue adhesive in experimental scleral buckling", Acta Ophthalmology Scand, Oct. 2001, pp. 506-508, vol. 79(5).
U.S. Appl. No. 60/550,132, filed Mar. 4, 2004.
U.S. Appl. No. 60/557,368, filed Mar. 29, 2004.
U.S. Appl. No. 60/564,858, filed Apr. 23, 2004.
U.S. Appl. No. 60/637,569, filed Dec. 20, 2004.

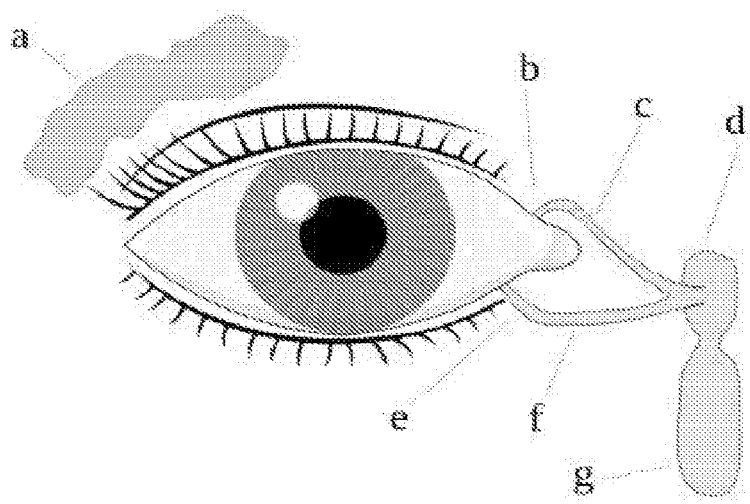

PUNCTAL PLUG AND BIOADHESIVES

REFERENCE TO RELATED APPLICATIONS

This application claims the benefit of U.S. Provisional Patent Application No. 62/239,006, filed Oct. 8, 2015, the contents of which are fully incorporated by reference herein.

BACKGROUND OF THE INVENTION

The invention concerns devices for intubation of the lacrimal duct of an eye for treatment of any of various disorders of the eye, including in particular "dry eye", also known as sicca syndrome.

As shown in FIG. 1, the lacrimal gland secretes tears which drain into the inferior nasal meatus via the lacrimal duct after moistening the ocular surface having the cornea and conjunctiva. The lacrimal duct consists of the upper punctum, lower punctum, vertical portion of the upper punctum, vertical portion of the lower punctum, boundary portion between the upper vertical and horizontal portions, boundary portion between the lower vertical and horizontal portions, upper horizontal portion, lower horizontal portion, common canaliculus, lacrimal sac, and nasolacrimal duct. The lower end of the nasolacrimal duct opens into the inferior nasal meatus.

Patients with dry eye have a deficiency of tears, which are very important for function and comfort of the eye. Dry eye symptoms include asthenopia, waking irritation, grittiness, foreign body sensation, scratchiness, soreness, difficulty to open the eyes in an air conditioned room, injection, burning, etc. In dry eye, tears drain away from the eye, more quickly than they should, via the lacrimal duct.

To suppress tear drainage, the upper punctum can be occluded using a punctal plug (sometimes referred to as a punctum plug, lacrimal punctum plug, or lacrimal insert) inserted into the upper punctum, and/or the lower punctum can be occluded using a punctal plug inserted into the lower punctum.

By blocking the upper punctum and lower punctum like this, tears are accumulated in the conjunctival sac, and in many cases dry eye symptoms improve.

Punctal plugs in current use are either "temporary" or "permanent". So-called temporary punctal plugs typically are simple tubular structures made of collagen or synthetic collagen, and they are designed to last for about ten days to about three months, over which time they dissolve or fall out. So-called permanent punctal plugs typically are more complex, contoured devices usually made of silicone, and, while they do not dissolve, they can cause irritation and frequently fall out. Examples of punctal plugs are described in U.S. Pat. No. 3,949,750 to Freeman; U.S. Pat. No. 5,283,063 to Freeman; U.S. Pat. No. 5,417,651 to Guena et al.; U.S. Pat. No. 6,027,470 to Mendius; U.S. Pat. No. 6,238,363 to Kurihashi; U.S. Pat. No. 6,290,684 to Herrick; U.S. Pat. No. 7,785,285 to Kurihashi; U.S. Pat. No. 8,439,865 to Lust et al.; U.S. Pat. No. 8,628,792 to Utkhede et al.; U.S. Pat. No. 8,795,711 to de Juan, Jr. et al.; and U.S. Pat. No. 8,821,457 to Beeley et al., the entire contents of all of which are incorporated herein by reference.

SUMMARY OF THE INVENTION

An aspect of the invention is a punctal plug comprising a body comprising a biodegradable polymer, wherein said biodegradable polymer is not collagen or synthetic collagen.

An aspect of the invention is a punctal plug comprising a body comprising a biocompatible elastic polymer, wherein said biocompatible elastic polymer is not silicone.

An aspect of the invention is an insertion device suitable for use in inserting or removing a punctal plug of the invention.

An aspect of the invention is a method of using a punctal plug, comprising the steps of applying a bioadhesive to a tissue-contacting outer surface of a punctal plug, thereby forming a bioadhesive-coated punctal plug; and inserting the bioadhesive-coated punctal plug into a punctum of an eye.

An aspect of the invention is a method of treating dry eye, comprising installing into a punctum opening of an eye of a subject in need thereof a punctal plug of the invention.

An aspect of the invention is a punctal plug, comprising a bioadhesive disposed on a surface oriented to contact tissue of a subject.

An aspect of the invention is a kit comprising a punctal plug and a bioadhesive. In certain embodiments, the punctal plug may be a punctal plug as described above.

An aspect of the invention is a method of treating an ophthalmological condition such as dry-eye, comprising inserting a bioadhesive into the punctum or the canaliculus.

An aspect of the invention is a kit comprising a bioadhesive and an applicator suitable for inserting the bioadhesive into the punctum or the canaliculus, or both.

BRIEF DESCRIPTION OF THE DRAWING

FIG. 1 depicts eye tear system anatomy. Indicated are (a), tear/lacrimal gland; (b), superior lacrimal punctum; (c), superior lacrimal canal; (d), tear/lacrimal sac; (e), inferior lacrimal punctum; (f), inferior lacrimal canal; (g), nasolacrimal canal.

DETAILED DESCRIPTION OF THE INVENTION

The invention provides a longer lasting version of a temporary punctal plug. Currently, temporary punctal plugs are made out of collagen or synthetic collagen. In accordance with the invention, a temporary plug with a longer useful life is constructed using a longer lasting biodegradable polymer.

So-called "permanent" punctal plugs are currently made out of silicone. In accordance with the invention, a permanent plug is made using another material such as a biocompatible polymer, preferably a biocompatible elastic polymer.

The invention further provides a punctal plug with a thin, contoured exposed edge possibly using silicone or another biocompatible polymer with malleable property that can mold to punctal anatomy. This punctal plug may or may not have bioadhesive attached.

A feature of certain embodiments of the invention is the use of a bioadhesive to keep the plug in place. This adhesive may be synthetic or natural.

In certain embodiments, the punctal plug has textured surface to promote its staying in place, e.g. a "shark skin" surface or a gecko *setae*-like surface.

The invention further provides a punctal plug with intracanalicular extension. The plug portion has any of the possible attributes just described. The intracanalicular extension can be a liquid-like, gelatinous, or semi-solid material that becomes more formed and mold to the canaliculus. It may or may not have a bioadhesive on its surface or within its structure. Existing expandable "smart plugs", which are strictly intracanalicular, have been plagued with problems because they migrate into the lacrimal sac and cause infections. In contrast, in this embodiment of the invention, the punctal plug portion keeps the intracanalicular portion from migrating into the lacrimal sac, and the canalicular portion helps prevent the plug from extruding from the punctum.

An aspect of the invention is a punctal plug comprising a body comprising a biodegradable polymer, wherein said biodegradable polymer is not collagen or synthetic collagen.

In certain embodiments, the biodegradable polymer is selected from poly(alpha-esters); polyglycolide; polylactide; polylactide-co-glycolide; polyhydroxyalkanoates; polycaprolactone; polypropylene fumarate; polyanhydrides; polyacetals; polyortho esters; polycarbonates; polyurethanes; polyphosphazenes; polyphosphoesters; polyester-ester; polyamide-ester; polyanhydride-ester; enzymatically degradable polymers; synthetic polyethers; polyethylene glycol (PEG); polypropylene glycol (PPG); PEGdiacrylate (PEGDA); PEGdimethacrylate (PEGDMA); PEGDA and PEGDMA with other acrylates and methacrylate; degradable polymer proteins and poly(amino acids) selected from elastin, elastin-like polypeptides, albumin, natural poly(amino acids), poly(y-glutamic acid), poly L-lysine, poly L-glutamic acid, poly aspartic acid, polysaccharides, hyaluronic acid methacrylate, hyaluronic acid chondroitin sulfate, and chitosan alginate; and any combination thereof. In certain embodiments, the biodegradable polymer excludes any one or more of poly(alpha-esters); polyglycolide; polylactide; polylactide-co-glycolide; polyhydroxyalkanoates; polycaprolactone; polypropylene fumarate; polyanhydrides; polyacetals; polyortho esters; polycarbonates; polyurethanes; polyphosphazenes; polyphosphoesters; polyester-ester; polyamide-ester; polyanhydride-ester; enzymatically degradable polymers; synthetic polyethers; polyethylene glycol (PEG); polypropylene glycol (PPG); PEGdiacrylate (PEGDA); PEGdimethacrylate (PEGDMA); PEGDA and PEGDMA with other acrylates and methacrylate; degradable polymer proteins and poly(amino acids) selected from elastin, elastin-like polypeptides, albumin, natural poly(amino acids), poly(y-glutamic acid), poly L-lysine, poly L-glutamic acid, poly aspartic acid, polysaccharides, hyaluronic acid methacrylate, hyaluronic acid chondroitin sulfate, and chitosan alginate.

An aspect of the invention is a punctal plug comprising a body comprising a biocompatible elastic polymer, wherein said biocompatible elastic polymer is not silicone.

In certain embodiments, the biocompatible elastic polymer is selected from Acrysof (copolymer of phenylethyl acrylate and phenylethyl methacrylate cross linked with butanediol diacrylate); natural and synthetic forms of amniotic membrane; degradable polymer proteins and poly(amino acids) selected from elastin, elastin-like polypeptides, albumin, natural poly(amino acids), poly(y-glutamic acid), poly L-lysine, poly L-glutamic acid, poly aspartic acid, polysaccharides, hyaluronic acid methacrylate, hyaluronic acid chondroitin sulfate, and chitosan alginate; Dow Corning elastomers; enzymatically degradable polymers; ester-based thermoplastic polyurethane elastomer (TPUR) compounds; ether-based thermoplastic polyurethane elastomer (TPUR) compounds; Hoya (cross linked copolymer of phenylethyl methacrylate and n-butyl acrylate, fluoroalkyl methacrylate); hydrogels; hydrophilic acrylics; hydrophobic acrylics (foldable and non-foldable); hydroxyethylmethacrylate (HEMA) hydrophilic polymer; methyl methacrylate; nylon; PEGDA and PEGDMA with other acrylates and methacrylate; PEGdiacrylate (PEGDA); PEGdimethacrylate (PEGDMA); poliglecaprone suture; poly(alpha-esters); polyacetals; polyamide-esters; polyamides; polyanhydride-esters; polyanhydrides; polycaprolactones; polycarbonates; polydioxanones; polyester urethanes; polyesters; polyether polyester copolymers; polyether urethanes; polyether-ester block copolymer thermoplastic elastomer (TEEE) compounds; polyethylene glycol (PEG); polyethylenes; polyglactin 910 suture; polyglycolic acid suture; polyglycolides; polyhydroxyalkanoates; polylactides; polylactide-co-glycolides; polymethylmethacrylate (PMMA); polyortho esters; polyphosphazenes; polyphosphoesters; polypropylenes; polypropylene fumarate; polypropylene glycol (PPG); polypropylene oxide; polytetrafluorethylene (Teflon); polyurethanes; RTP Co. thermoplastic elastomers; saturated styrenic block copolymer thermoplastic elastomers; SILASTIC® (medical adhesive silicone, Dow Corning); silicone hydrogels; silk; synthetic polyethers; Tecnis acrylic (copolymer of ethyl acrylate ethyl methacrylate, 2,2,2-trifluorethyl methacrylate, cross linked with ethylene glycol dimethacrylate); thermoplastic polyolefin elastomer (TEO) compounds; and thermoplastic vulcanizate (TPV) compounds.

In certain embodiments, the biocompatible elastic polymer excludes any one or more of Acrysof (copolymer of phenylethyl acrylate and phenylethyl methacrylate cross linked with butanediol diacrylate); natural and synthetic forms of amniotic membrane; degradable polymer proteins and poly(amino acids) selected from elastin, elastin-like polypeptides, albumin, natural poly(amino acids), poly(y-glutamic acid), poly L-lysine, poly L-glutamic acid, poly aspartic acid, polysaccharides, hyaluronic acid methacrylate, hyaluronic acid chondroitin sulfate, and chitosan alginate; Dow Corning elastomers; enzymatically degradable polymers; ester-based thermoplastic polyurethane elastomer (TPUR) compounds; ether-based thermoplastic polyurethane elastomer (TPUR) compounds; Hoya (cross linked copolymer of phenylethyl methacrylate and n-butyl acrylate, fluoroalkyl methacrylate); hydrogels; hydrophilic acrylics; hydrophobic acrylics (foldable and non-foldable); hydroxyethylmethacrylate (HEMA) hydrophilic polymer; methyl methacrylate; nylon; PEGDA and PEGDMA with other acrylates and methacrylate; PEGdiacrylate (PEGDA); PEGdimethacrylate (PEGDMA); poliglecaprone suture; poly(alpha-esters); polyacetals; polyamide-esters; polyamides; polyanhydride-esters; polyanhydrides; polycaprolactones; polycarbonates; polydioxanones; polyester urethanes; polyesters; polyether polyester copolymers; polyether urethanes; polyether-ester block copolymer thermoplastic elastomer (TEEE) compounds; polyethylene glycol (PEG); poly ethylenes; polyglactin 910 suture; polyglycolic acid suture; polyglycolides; polyhydroxyalkanoates; polylactides; polylactide-co-glycolides; polymethylmethacrylate (PMMA); polyortho esters; polyphosphazenes; polyphosphoesters; polypropylenes; polypropylene fumarate; polypropylene glycol (PPG); polypropylene oxide; polytetrafluorethylene (Teflon); polyurethanes; RTP Co. thermoplastic elastomers; saturated styrenic block copolymer thermoplastic elastomers; SILASTIC® (medical adhesive silicone, Dow Corning); silicone hydrogels; silk; synthetic polyethers; Tecnis acrylic (copolymer of ethyl acrylate ethyl methacrylate, 2,2,2-trifluorethyl methacrylate, cross linked with ethylene glycol dimethacrylate); thermoplastic polyolefin elastomer (TEO) compounds; and thermoplastic vulcanizate (TPV) compounds.

In accordance with any of the foregoing aspects and embodiments, in certain embodiments the body comprises a flared proximal end.

In accordance with any of the foregoing aspects and embodiments, in certain embodiments the body comprises a flared midsection.

In accordance with any of the foregoing aspects and embodiments, in certain embodiments the body comprises a flared distal end.

In accordance with any of the foregoing aspects and embodiments, in certain embodiments the body comprises a valve or septum through which a material can be injected or introduced into the punctal plug.

In accordance with any of the foregoing aspects and embodiments, in certain embodiments the punctal plug further comprises a bioadhesive disposed on a surface oriented to contact tissue of a subject.

An aspect of the invention is a punctal plug, comprising a bioadhesive disposed on a surface oriented to contact tissue of a subject. The punctal plug may be a punctal plug as described above, or may be any other punctal plug known to those of skill in the art. In certain embodiments, the punctal plug comprises a body and a bioadhesive, wherein the bioadhesive is disposed on a tissue-contacting outer surface of the body. In certain embodiments, the punctal plug comprises a body comprising a biodegradable polymer, wherein said biodegradable polymer is collagen or synthetic collagen. In certain embodiments, the punctal plug comprises a body comprising a biodegradable polymer, wherein said biodegradable polymer is not collagen or synthetic collagen. In certain embodiments, the punctal plug comprises a body comprising a biocompatible elastic polymer, wherein said biocompatible elastic polymer is silicone. In certain embodiments, the punctal plug comprises a body comprising a biocompatible elastic polymer, wherein said biocompatible elastic polymer is not silicone.

In certain embodiments, the bioadhesive is selected from the bioadhesives described herein, such as spider web-based bioadhesive, gecko lizard-based bioadhesive, fibrin glue, gelatin-based glue, gelatin-resorcinol-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL®), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), citrate-enabled mussel-inspired bioadhesives (iCMBA), and any combination thereof. In certain embodiments, the bioadhesive can exclude any one or more bioadhesives selected from spider web-based bioadhesive, gecko lizard-based bioadhesive, fibrin glue, gelatin-based glue, gelatin-resorcin-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), and citrate-enabled mussel-inspired bioadhesives (iCMBA).

In certain embodiments, the bioadhesive is a mussel adhesive protein (MAP), synthetic MAP, or a MAP-inspired polymer such as are described in U.S. Pat. No. 8,673,286 to Messersmith et al., and WO 2013/123946 to Aarhus Universitet, the entire contents of which are incorporated herein by reference. As disclosed in Messersmith et al., MAPs are remarkable underwater adhesive materials secreted by certain marine organisms which form tenacious bonds to the substrates upon which they reside. During the process of attachment to a substrate, MAPs are secreted as adhesive fluid precursors that undergo a crosslinking or hardening reaction which leads to the formation of a solid adhesive plaque. One of the unique features of MAPs is the presence of L-3-4-dihydroxyphenylalanine (DOPA), an unusual amino acid which is believed to be responsible for adhesion to substrates through several mechanisms that are not yet fully understood. The observation that mussels adhere to a variety of surfaces in nature (metal, metal oxide, polymer) led to a hypothesis that DOPA-containing peptides can be employed as the key components of synthetic medical adhesives. Messersmith et al. specifically discloses DOPA (and related multihydroxyphenyl derivatives)-functionalized polyalkylene oxide materials that are useful as adhesives.

In certain embodiments, the bioadhesive is biodegradable. For example, the bioadhesive may be selected from natural and synthetic forms of amniotic membrane, fibrin glue, MAP, synthetic MAP, or synthetic MAP coated by DOPA-functionalized PEG and PCL. In other embodiments, the bioadhesive may be an isocyanatoethylmethacrylate-based bioadhesive (as described in Ferreira et al., Int J. Pharm, 2008 Mar. 20; 352(1-2): 172-81; a biodegradable urethane-based bioadhesive (as described in J Mater Sci Mater Med. 2008 January; 19(1): 111-20); or a poly-dihydroacetate-based bioadhesive (as described in Singh et al., J. Am. Col. Surgeons, September 2008 Volume 207, Issue 3, Supplement, Page S64).

In certain embodiments, the bioadhesive comprises a textured surface, e.g. a "shark skin" surface or a gecko setae-like surface. In certain embodiments, the bioadhesive imparts a textured surface, e.g. a "shark skin" surface or a gecko setae-like surface.

In certain embodiments, the bioadhesive is applied to the punctal plug at the time of installation of the plug into a subject.

In accordance with any of the foregoing aspects and embodiments, the punctal plug further comprises a core or reservoir at least partially within the body of the punctal plug, wherein the core or reservoir comprises a therapeutic agent.

An aspect of the invention is an insertion device suitable for use in inserting or removing a punctal plug of the invention. In certain embodiments, the punctal plug comprises an opening or blind hole constructed and arranged so as to accept an insertion device. The insertion device is constructed and arranged so as to releasably engage the punctal plug for purposes of inserting the punctal plug into a punctum opening of an eye. The insertion device can be constructed and arranged so as to releasably engage the punctal plug for purposes of removing the punctal plug from a punctum opening of an eye.

An aspect of the invention is a kit comprising a punctal plug and a bioadhesive. In certain embodiments, the punctal plug may be a punctal plug as described above.

In certain embodiments, the bioadhesive is selected from the bioadhesives described herein, such as spider web-based bioadhesive, natural and synthetic forms of amniotic membrane, fibrin glue, gelatin-based glue, gelatin-resorcinol-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), citrate-enabled mussel-inspired bioadhesives (iCMBA), MAP-inspired polymers, and any combination thereof. In certain embodiments, the bioadhesive can exclude any one or more bioadhesives selected from spider web-based bioadhesive, gecko lizard-based bioadhesive, natural and synthetic forms of amniotic membrane, fibrin glue, gelatin-based glue, gelatin-resorcin-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), citrate-enabled mussel-inspired bioadhesives (iCMBA), and MAP-inspired polymers.

In certain embodiments, the bioadhesive is biodegradable. For example, the bioadhesive may be selected from natural and synthetic forms of amniotic membrane, fibrin glue, MAP, synthetic MAP, or synthetic MAP coated by DOPA-functionalized PEG and PCL. In other embodiments, the bioadhesive may be an isocyanatoethylmethacrylate-based bioadhesive (as described in Ferreira et al., Int J. Pharm, 2008 Mar. 20; 352(1-2): 172-81); a biodegradable urethane-based bioadhesive (as described in J Mater Sci Mater Med. 2008 January; 19(1): 111-20); or a poly-dihydroacetate-based bioadhesive (as described in Singh et al., J. Am. Col. Surgeons, September 2008 Volume 207, Issue 3, Supplement, Page S64).

The punctal plug may be any suitable punctal plug known to those of skill in the art. Preferably, the punctal plug is a punctal plug of the invention.

An aspect of the invention is a method of using a punctal plug, comprising the steps of applying a bioadhesive to a tissue-contacting outer surface of a punctal plug, thereby forming a bioadhesive-coated punctal plug; and inserting the bioadhesive-coated punctal plug into a punctum of an eye.

In certain embodiments, the bioadhesive is selected from the bioadhesives described herein, such as spider web-based bioadhesive, gecko lizard-based bioadhesive, natural and synthetic forms of amniotic membrane, fibrin glue, gelatin-based glue, gelatin-resorcinol-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), citrate-enabled mussel-inspired bioadhesives (iCMBA), MAP-inspired polymers, and any combination thereof. In certain embodiments, the bioadhesive can exclude any one or more bioadhesives selected from spider web-based bioadhesive, gecko lizard-based bioadhesive, natural and synthetic forms of amniotic membrane, fibrin glue, gelatin-based glue, gelatin-resorcin-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), citrate-enabled mussel-inspired bioadhesives (iCMBA), and MAP-inspired polymers.

In certain embodiments, the bioadhesive is biodegradable. For example, the bioadhesive may be selected from natural and synthetic forms of amniotic membrane, fibrin glue, MAP, synthetic MAP, or synthetic MAP coated by DOPA-functionalized PEG and PCL. In other embodiments, the bioadhesive may be an isocyanatoethylmethacrylate-based bioadhesive (as described in Ferreira et al., Int J. Pharm, 2008 Mar. 20; 352(1-2): 172-81); a biodegradable urethane-based bioadhesive (as described in J Mater Sci Mater Med. 2008 January; 19(1): 111-20); or a poly-dihydroacetate-based bioadhesive (as described in Singh et al., J. Am. Col. Surgeons, September 2008 Volume 207, Issue 3, Supplement, Page S64).

In certain embodiments, the punctal plug is a punctal plug of the invention.

In certain embodiments, the punctal plug is a prior art punctal plug.

An aspect of the invention is a method of treating an ophthalmological condition such as dry-eye, comprising inserting a bioadhesive into the punctum or the canaliculus. As a result, fluid flow through the punctum or the canaliculus is blocked. This technique allows treatment of dry eye without using a physical punctal plug. The punctum or canaliculus, or both, can be directly glued shut. This avoids the need to manufacture and sterilize the plug itself, and avoids the risk of the plug falling out.

The bioadhesive may be inserted into the punctum or canaliculus by any suitable method. In some embodiments, the bioadhesive is applied to an applicator, and the applicator is then used to insert the bioadhesive into the punctum or canaliculus. In some embodiments, the bioadhesive is contained within a syringe or squeeze ampule, which is used to insert the bioadhesive into the punctum or canaliculus. If the bioadhesive is contained within a syringe or other similar device, it may be prefilled or filled just prior to insertion.

In some embodiments, the bioadhesive may be selected from the bioadhesives described herein, such as spider web-based bioadhesive, gecko lizard-based bioadhesive, natural and synthetic forms of amniotic membrane, fibrin glue, gelatin-based glue, gelatin-resorcinol-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), citrate-enabled mussel-inspired bioadhesives (iCMBA), MAP-inspired polymers, and any combination thereof. In certain embodiments, the bioadhesive can exclude any one or more bioadhesives selected from spider web-based bioadhesive, gecko lizard-based bioadhesive, natural and synthetic forms of amniotic membrane, fibrin glue, gelatin-based glue, gelatin-resorcin-formaldehyde/glutaraldehyde (GRF or GRFG), glutaraldehyde glyoxal, albumin-glutaraldehyde, cyanoacrylate, 2-octylcyanocrylate, n-butyl-2-cyanoacrylate (INDERMIL), polyethylene glycol (PEG)-based hydrogel sealant, urethane-based adhesive, mussel adhesive protein (MAP), synthetic MAP, synthetic MAP coated by DOPA-functionalized PEG and polycaprolactone (PCL), citrate-enabled mussel-inspired bioadhesives (iCMBA), and MAP-inspired polymers.

In certain embodiments, the bioadhesive is biodegradable. For example, the bioadhesive may be selected from natural and synthetic forms of amniotic membrane, fibrin glue, MAP, synthetic MAP, synthetic MAP coated by DOPA-functionalized PEG and PCL, or MAP-inspired polymers. In other embodiments, the bioadhesive may be an isocyanatoethylmethacrylate-based bioadhesive (as described in Ferreira et al., Int J. Pharm, 2008 Mar. 20; 352(1-2): 172-81; a biodegradable urethane-based bioadhesive (as described in J Mater Sci Mater Med. 2008 January; 19(1): 111-20); or a poly-dihydroacetate-based bioadhesive (as described in Singh et al., J. Am. Col. Surgeons, September 2008 Volume 207, Issue 3, Supplement, Page S64).

An aspect of the invention is a kit comprising a bioadhesive and an applicator suitable for inserting the bioadhesive into the punctum or the canaliculus, or both. In certain embodiments, the bioadhesive is a bioadhesive as described above. In certain embodiments, the bioadhesive is biodegradable, and may be selected from the biodegradable bioadhesives described above. In certain embodiments, the kit comprises two applicators: one suitable for inserting the bioadhesive into the punctum and one suitable for inserting the bioadhesive into the canaliculus.

The devices may be used to deliver corticosteroids including dexamethasone sodium phosphate, dexamethasone, fluoromethalone, fluoromethalone acetate, loteprednol etabonate, prednisolone acetate, prednisolone sodium phosphate, medrysone, rimexolone, and fluocinolone acetonide. The devices may be used to deliver non-steroidal anti-inflammatory agents including flurbiprofen sodium, suprofen, diclofenac sodium, ketorolac tromethamine, cyclosporine, rapamycin, methotrexate, azathioprine, and bromocriptine.

EXAMPLES

Having now described the present invention in detail, the same will be more clearly understood by reference to the following examples, which are included herewith for purposes of illustration only and are not intended to be limiting of the invention.

Example 1

A punctal plug is manufactured out of a biomaterial substantially as described herein. In one embodiment, the punctal plug is a "temporary" punctal plug. In one embodiment, the punctal plug is a "permanent" punctal plug.

Example 2

A punctal plug of Example 1 is coated with a bioadhesive substantially as described herein prior to insertion of the punctal plug into a punctum opening of an eye. The bioadhesive coating is applied by any one or more of painting, dipping or submerging, rolling, or the like, with or in the bioadhesive. The punctal plug is optionally held in place by the operator long enough for the bioadhesive to cure or adhere to tissue sufficiently to stabilize the plug in place. Preferably the time required for such curing or adhering is about 15 seconds to about 5 minutes.

Example 3

A prior art punctal plug is coated with a bioadhesive substantially as described herein prior to insertion of the punctal plug into a punctum opening of an eye. The bioadhesive coating is applied by any one or more of painting, dipping or submerging, rolling, or the like, with or in the bioadhesive. The punctal plug is optionally held in place by the operator long enough for the bioadhesive to cure or adhere to tissue sufficiently to stabilize the plug in place. Preferably the time required for such curing or adhering is about 15 seconds to about 5 minutes.

Example 4

A syringe is pre-filled with a bioadhesive substantially as described herein. The syringe is used to insert the bioadhesive into the punctum and canaliculus of a patient's eye, thereby sealing the punctum and the canaliculus. Preferably the bioadhesive cures, such that fluid transmission through the punctum and canaliculus is blocked, within about 15 seconds to about 5 minutes.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

What is claimed is:

1. A method of treating an ophthalmological condition comprising:
   (i) inserting a temporary lacrimal insert comprising a non-steroidal anti-inflammatory agent, a punctal plug portion and an intracanalicular portion into a punctum of an eye; wherein the punctal plug portion is configured to keep the intracanalicular portion from migrating into the lacrimal sac and wherein the intracanalicular portion is configured to prevent the punctal plug portion from extruding from the punctum; wherein the intracanalicular portion molds to a shape of a canaliculus; wherein the lacrimal insert comprises a biodegradable polymer; and wherein the time required for the lacrimal insert to adhere to tissue in the punctum sufficiently to stabilize the lacrimal insert in place is about 15 seconds to about 5 minutes; wherein the biodegradable polymer is not collagen or synthetic collagen; wherein the biodegradable polymer is selected from polyethylene glycol; polyethylenes; polyglycolides; polyhydroxyalkanoates; or any combination thereof; and wherein the lacrimal insert further comprises polyethylene glycol based hydrogel sealant disposed on a body surface oriented to contact the tissue of the punctum of a subject; and
   (ii) occluding the punctum with the inserted lacrimal insert.

2. The method of claim 1, wherein the non-steroidal anti-inflammatory agent is cyclosporine.

* * * * *